United States Patent [19]

Shimura et al.

[11] Patent Number: 4,957,437
[45] Date of Patent: Sep. 18, 1990

[54] ARTIFICIAL TOOTH

[75] Inventors: Kaizo Shimura, Yokosuka; Hiroyasu Takeuchi, Tokorozawa; Masahiro Hirano, Yokozemachi; Yohji Imai, Chiba, all of Japan

[73] Assignee: Mitsubishi Mining & Cement Co., Ltd., Tokyo, Japan

[21] Appl. No.: 311,539

[22] Filed: Feb. 16, 1989

[30] Foreign Application Priority Data

Feb. 23, 1988 [JP] Japan .................................. 63-38752

[51] Int. Cl.$^5$ ............................................. A61C 13/28
[52] U.S. Cl. .................... 433/169; 433/174; 433/201.1
[58] Field of Search ............... 433/169, 173, 174, 175, 433/176, 201.1

[56] References Cited

U.S. PATENT DOCUMENTS 3,955,280 5/1976 Sneer ...................................... 433/169
4,324,550 4/1982 Reuther et al. ....................... 433/169

FOREIGN PATENT DOCUMENTS 2031450 4/1980 United Kingdom ................ 433/173

Primary Examiner—Cary E. Stone
Attorney, Agent, or Firm—Charles E. Baxley

[57] ABSTRACT

An artifical tooth comprises a contacting member formed of a composite material having compatibility with living tissues and diaposed at an outer portion of the artificial tooth to be contacted with alveolar bone, a metal base member having an opening therein and disposed inside of and attached to the contacting member, a metal post inserted into the opening of the metal base member and at least two elastic buffer members disposed in a space between the metal base member and the metal post. The composite material having compatibility with living tissues contains 40 to 95% by weight of a calcium phosphate compound and 60 to 5% by weight of an organic polymer. Each of the elastic buffer members is spaced apart for movably receiving the metal post by which pressure imposed upon the artificial tooth is transmitted.

10 Claims, 1 Drawing Sheet

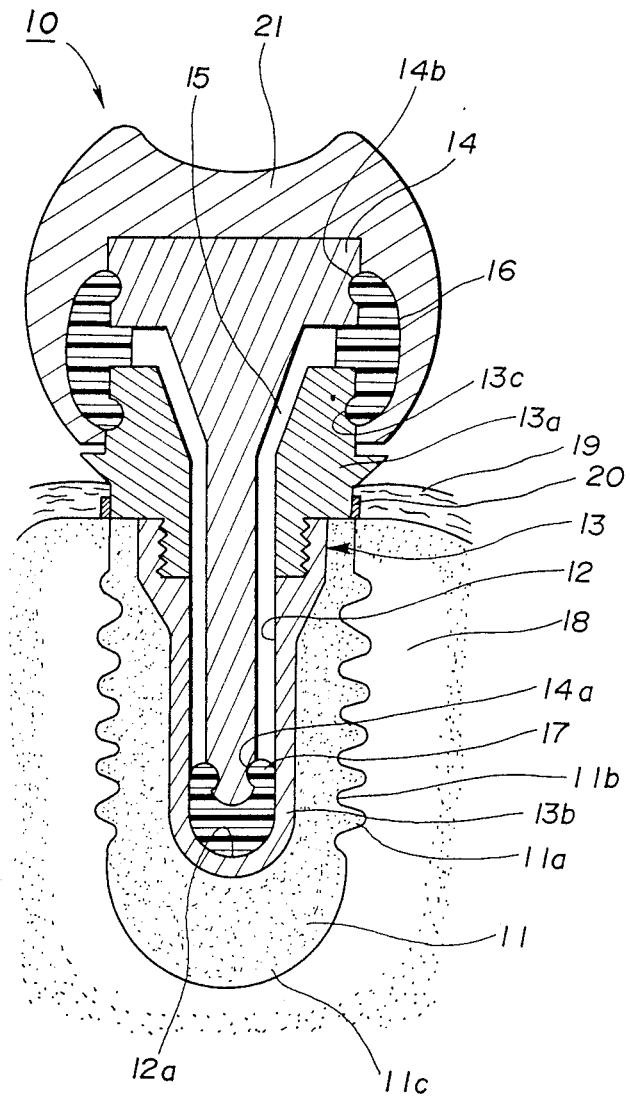
FIG.

ARTIFICIAL TOOTH

BACKGROUND OF THE INVENTION

This invention relates to an artificial tooth for substituting a natural tooth lost by dental diseases Up to the present, metals such as titanium and ceramics such as alumina or hydroxyapatite, have been utilized as the materials for artificial teeth. However, the artificial teeth made of metals present problems in biocompatibility since they tend to be attacked and dissolved in the living tissues, while being higher in hardness and modulus of elasticity than those of the bone tissue. The artificial teeth made of ceramics also present problems with respect to brittleness, hardness and machinability.

An artificial tooth comprising a metal core and a ceramic coating applied to the core has also been produced and offered to the market. However, these artificial teeth have not been used extensively because of the rather weak connection between the metal and the ceramics.

For overcoming the above inconveniences, there has recently been evolved an artificial tooth including an outer contacting portion which is formed of a composite material exhibiting biocompatibility and which is disposed in contact with the alveolar bone, a metal member disposed at the inner side of the contacting member and having an opening, a metal post introduced into the opening and an elastic buffer member adapted for filling in a gap between the metal post and the metal member (Japanese Unexamined Patent Publication No. 152449/1987). This artificial tooth has a drawback that it does not necessarily produce a sufficient buffer action such that the extent of possible movement of the metal post under the tooth pressure applied to the post is less than that in the natural tooth, while the artificial tooth cannot be produced in a configuration which will exhibit sufficient strength and sufficient extent of movement of the metal post.

SUMMARY OF THE INVENTION

It is a principal object of the present invention to provide an artificial tooth having superior compatibility with living tissues and having high strength and a modulus of elasticity comparable with those of the bone tissue of the living body.

It is another object of the present invention to provide an artificial tooth having a sufficient extent of movement and exhibiting properties close to those of a natural tooth.

It is a further object of the present invention to provide an artificial tooth that can be manufactured easily and that can be used for prolonged time by substitution of damaged or used-up component parts.

It is a further object of the present invention to provide an artificial tooth which makes it possible to perform an operation that will rarely cause inflammation in the gingiva.

It is yet another object of the present invention to provide an artificial tooth which makes it possible to reunite the gingival mucosa or epithelial tissue and the artificial tooth when the adhesion therebetween is lost or injured.

The above and other objects of the present invention will become apparent from the following description.

In accordance with the present invention, there is provided an artificial tooth comprising a contacting member made of a composite material having compatibility with living tissues and disposed at an outer portion of the artificial tooth to be contacted with alveolar bone, a metal base member having an opening therein and disposed inside of and attached to the contacting member, a metal post inserted into the opening of the metal base member and at least two elastic buffer members disposed in a space between the metal base member and the metal post, the composite material having compatibility with living tissues containing 40 to 95% by weight of a calcium phosphate compound and 60 to 5% by weight of an organic polymer, each of the elastic buffer members being spaced apart for movably receiving the metal post by which pressure imposed upon the artificial tooth is transmitted.

BRIEF DESCRIPTION OF THE DRAWINGS

The single FIGURE is a diagrammatic sectional view showing an artificial tooth according to the present invention.

PREFERRED EMBODIMENTS OF THE INVENTION

By referring to the accompanying drawings, the present invention will be explained in more detail.

An artificial tooth 10 according to the present invention includes a contacting member 11 made of a composite material having compatibility with living tissues and disposed at an outer portion of the artificial tooth 10 to be contacted with alveolar bone 18, a metal base member 13 having an opening 12 therein and disposed inside of and attached to the contacting member 11, a metal post 14 inserted into the opening 12 of the metal base member 13 and at least two elastic buffer members 16, 17 spaced apart each other and disposed in a space 15 between the metal base member 13 and the metal post 14.

Inasmuch as the contacting member 11 having compatibility with living tissues according to the present invention contacts directly with the alveolar bone 18, a composite material containing 40 to 95% by weight of a calcium phosphate compound having compatibility with living tissues and 60 to 5% by weight of an organic polymer is employed as the composite material constituting the contacting member 11. With the contents of the calcium phosphate compound less than 40% by weight, growth of new bone is retarded and it takes much time until the composite material is unified with the alveolar bone. With the contents of the calcium phosphate compound in excess of 95% by weight, difficulties are presented in machining and hence in the industrial mass production of artificial teeth. It is noted that, within the range of contents of 40 to 95% by weight of the calcium phosphate compound, a larger amount of the new bone is formed around the artificial tooth material and the physical properties of the artificial tooth closer to those of natural bone are obtained. In addition, the artificial tooth exhibits the modulus of elasticity close to that of the natural tooth and excellent machinability so that the artificial tooth of a predetermined size may be mass-produced and hence the dental operation is facilitated.

Examples of the aforementioned calcium phosphate compounds include tricalcium phosphate, hydroxyapatite, tetracalcium phosphate, oxyapatite, calcium pyrophosphate, fluoroapatite, a compound in which hydroxyl groups of hydroxyapatite are partly substituted by fluorine ions, brushite ($CaHPO_4.2H_2O$) and a mixture thereof. Among these calcium phosphate compounds, one or a mixture of two or more of those exhibiting a faster rate of formation of new bone, that is, tricalcium phosphate, hydroxyapatite, fluoroapatite or tetracalcium phosphate, are preferably employed. Above all, hydroxyapatite has the fastest rate of formation of new bone and therefore is most preferred among these compounds. The most preferred is hydroxyapatite obtained upon heat treatment at a temperature of not lower than 500° C., desirably not lower than 700° C. since it has an outstandingly high rate of formation of new bone. Although there is no upper limit temperature for heat treatment, hydroxyapatite starts to be decomposed at too high a temperature so that heat treatment should be carried out at lower than the decomposition temperature of hydroxyapatite. The calcium phosphate compounds that may be used in the present invention may either artificially synthesized compounds synthesized by known methods, such as the wet, dry or hydrothermal method, or compounds of natural origin obtained from human or animal bone. The calcium phosphate compounds used in the present invention may be powdered, granular or in the form of a porous body, on the condition that the compounds are miscible with monomers of the organic polymers.

There is no specific limitation to the organic polymers, on the condition that the polymers are not toxic to the living body and exhibit affinity with the calcium phosphate compounds. Thus, for example, carboxylic acid type polymers, such as polylactic acid or polyglycolic acid, carboxylate type polymers such as polymethylmethacrylate, abbreviated hereinafter to PMMA or poly(trifluoroethyl methacrylate), abbreviated hereinafter to PTFEMA, or olefinic polymers, such as polyethylene or polypropylene. Among these polymers, PMMA and PTFEMA exhibit higher affinity with calcium phosphate compounds and high strength and hence are particularly preferred. Above all, PTFEMA exhibits the highest affinity with calcium phosphate compounds and hence is most preferred.

The composite material may be produced by mixing and stirring a paste containing the polymer and the monomer of the organic polymer with the calcium phosphate compound and polymerizing the mixture by heating.

The composite material employed in the present invention is endowed with properties indispensable to the artificial tooth 10, that is, compatibility with living tissues, elasticity and machinability of the tooth material. Although the contacting member 11 may have a smooth outer surface, an indented surface presenting alternate projections 11a and recesses 11b as shown in the figure is preferred since the stress produced during mastication is distributed and released due to the increased bonding area between the composite material and the new bone, while the load applied to the bone tissues is reduced. The helical configuration of the projections 11a and the recesses 11b is most desirable since the artificial tooth 10 can be secured positively as soon as it is buried in the alveolar bone 18. Although the bottom section 11c of the contacting member 11 may be formed as a flat surface, a hemispherical shape of the bottom 11c as shown in the figure is most preferred since it promotes distribution of the stress during mastication.

The artificial tooth 10 of the present invention is provided with the metal base member 13 disposed inside of the contacting member 11 and having the opening 12 and the metal post 14 introduced into the opening 12. The metal base member 13 and the metal post 14 may be formed of known biocompatible metal materials, such as titanium, cobalt-chromium alloy or stainless steel (type 316L), as long as the metals satisfy the conditions of strength and hardness required of the artificial tooth 10. The metal base member 13 may be of integral or split type, as long as it is provided with the opening 12 by which the metal post 14 can be introduced into the inside of the metal base member 13. If the metal base member 13 is of split type, the metal base member 13 may be formed by an upper section 13a and a lower section 13b, as shown in the figure, these upper and lower sections 13a, 13b being connected together by any methods known in the art. When the split type metal base member 13 is employed, the operation of embedding the artificial tooth 10 of the present invention is performed as a two step type operation, namely, a first step of embedding the contacting member 11 and the lower section 13b completely in the alveolar bone 18, covering the contacting member 11 and the lower section 13b with gingival mucosa 19 and allowing them to be completely unified to the bone, and a second step of performing a dental operation for removably connecting and securing the upper section 13a and the metal post 14 to the lower member 13b such as by threaded connection. The split type metal base member 13 is particularly preferred since bacterial infection and funnel-shaped absorption of the alveolar bone around the embedded artificial tooth 10 may be prevented by such operation and the parts can be exchanged easily whenever it is necessary to exchange them due to damage or prolonged usage of the artificial tooth. It is preferred that the portion of the metal base member 13 contacting with the gingival mucosa 19 be as smooth as possible. A high polymer biocompatible material 20, such as collagen or fibronectin, which is placed at the portion of the metal base member 13 contacting with the gingival mucosa 19 is highly effective to prevent gingivitis. The material 20 is preferably affixed to the lower region of contact between the metal base member 13 and the gingival mucosa 19 such as by plasma polymerization. The metal base member 13 and the metal post 14 may be fabricated by any known methods such as turning or electric discharge processing.

According to the present invention, two or more buffer members 16, 17 are placed in a space 15 between the metal base member 13 and the metal post 14 in a spaced apart relation from each other, in such a manner that the metal post 14 adapted to transmit the tooth pressure applied to the artificial tooth 10 during mastication may be movably supported by the buffer members 16, 17, in other words, that the artificial tooth 10 will display the properties close to those of the natural tooth to procure a sufficient extent of movement of the metal post 14. Although the location and the number of the elastic buffer members 16, 17 may be selected optionally depending on the position of the tooth under treatment and the set of teeth, the buffer members may be placed at any positions in the gap or void between the metal base member 13 and the metal post 14, as long as a sufficient buffer action with respect to the tooth pressure may be achieved However, for procuring a sufficient extent of movement of the metal post 14, the elastic buffer members 16, 17 need be positioned at a spaced apart relation so that a gap or void may be maintained in the space 15. When the elastic buffer members 16, 17 are arranged in this manner, a sufficient extent of movement of the metal post 14 and a sufficient buffer action may be achieved. Although no specific limitation is placed to the shape of the elastic buffer member 17, it may be shaped so as to be received within a recess 14a formed at the foremost part of the metal post 14 at a lowermost portion 12a of the opening 12 of the metal base member 13, as shown in the figure. Also a recess 14b may be formed at an upper portion of the metal post 14, while a similar recess 13c may be formed in the upper section 13a of the metal base member 13, and the ring-shaped elastic buffer member 16 may be fitted in these recesses 13c, 14b as shown in the figure, in such a manner that the buffer member 16 not only performs the buffer action but also plays the role of connecting the metal base member 13 to the metal post 14 to each other. With the use of the elastic buffer members 16, 17, also adapted for interconnecting the component parts of the artificial tooth, the dimensional tolerance for the metal base member 13 and the metal post 14 may be less strict than in the conventional tooth, so that the designing and manufacture may be facilitated. There is no specific limitation to the location of the elastic buffer members 16, 17 adapted for connecting the component parts of the artificial tooth, or to the manner of connecting these component parts by the elastic buffer members 16, 17.

As the elastic buffer materials employed in accordance with the present invention, synthetic rubbers, such as polyurethane rubber, polyfluoroethylene rubber or fluorine type rubber, or silicone rubber, having Young's modulus of 2 to 250 kg/cm$^2$ and desirably 40 to 180 kg/cm$^2$, are preferably employed. Practically any elastic material having durability and high strength may be employed. The buffer materials having different values of the modulus of elasticity may be employed depending on the locations in which the buffer members 16, 17 are placed within the space 15 for realizing the desired delicate buffer action with respect to the tooth pressure.

According to the present invention, the contacting member 11 and the metal base member 13 can be affixed to each other by a commercial dental adhesive, such as methyl methacrylate type adhesives, sold by Morita Co. Ltd. under the trade name of "Superbond C & B". The elastic buffer members 16, 17 between the metal base member 13 and the metal post 14 may be coated directly on the surfaces of the metal base member 13 and/or the metal post 14 or may be contoured specifically as described hereinabove for form-locking and fitting to the metal base member 13 and the metal post 14. A tooth crown 21 is affixed to the metal post 14 using the aforementioned adhesive.

The artificial tooth according to the present invention is superior in compatibility with living tissues and has high strength and a sufficient extent of movement so that it exhibits the properties close to those of the natural tooth. Also it is easy to manufacture and can be employed for extended time subject to exchange of damaged or used-up components. Moreover, the artificial tooth of the present invention lends itself to facilitated dental operations, while it is effective to prevent gingivitis.

EXAMPLES OF THE INVENTION

The present invention will be explained in more detail with reference to an Example and a Comparative Example. However, these Examples are by way of illustration only and are not intended to limit the scope of the invention.

EXAMPLE 1

As shown in the figure, a contacting member 11 formed of a composite material containing 78% by weight of hydroxyapatite and 22% by weight of PTFEMA and a lower section 13b of the metal base member 13 formed of titanium were affixed together. The resulting assembly was filled in a portion of a tremolar tooth of a dog directly contacting with the alveolar bone 18 and was buried therein so that the upper edge of the assembly was flush with the upper edge of the bone 18. The assembly thus buried was then covered completely with a gingival mucosa 19. After the contacting member 11 and the alveolar bone 18 were unified together, the gingival mucosa 19 was opened and an upper member section 13a of the metal base member 13 was threadedly connected to the lower section 13b of the metal base member 13. A piece of collagen 20 was previously affixed by plasma polymerization to the upper section 13a so that the piece of collagen 20 as the high molecular biomaterial was placed between the upper section 13a and the gingival mucosa 19 and intimately contacted with the gingival mucosa 19.

An elastic buffer member 17 was fitted into a recess 14a of the metal post 14 which was then introduced in this state into the opening 12 of the metal base member 13. After the two projections on the ring-shaped elastic buffer member 16 were fitted into an annular recess 14b in the metal post 14 and into an annular recess 13c of the upper section 13a, the upper section 13a and the metal post 14 were interconnected by the ring-shaped elastic buffer member 16. A tooth crown 21 was finally applied to the metal post 14.

As shown in the figure, a space 15 was formed between the metal base member 13 and the metal post 14. As a result, satisfactory occlusion and the feel similar to that of a natural tooth were obtained. An X-ray inspection has revealed that the alveolar bone 18 and the artificial tooth 10 were unified together and there occurred no funnel-shaped absorption.

COMPARATIVE EXAMPLE 1

As elastic member was placed and filled in a space between an integral metal base member (no split type as in Example 1) and a metal post so that no space exists therebetween to thus form an artificial tooth. The tooth was buried by a one-step operation instead of by a dual-step operation as in Example 1 since the dual step dental operation could not be performed. Sufficient pressure releasing effect could not be obtained, such that, upon X-ray analysis, funnel-shaped absorption was seen to have taken place in the alveolar bone. Ultimately, the artificial tooth was dropped off.

Although the present invention has been described with reference to the specific example, it should be understood that various modifications and variations can be easily made by those skilled in the art without departing from the spirit of the invention. Accordingly, the foregoing disclosure should be interpreted as illustrative only and is not to be interpreted in a limiting sense. The present invention is limited only by the scope of the following claims.

What is claimed is:

1. An artificial tooth comprising a contacting member formed of a composite material having compatibility with living tissues and disposed at an outer portion of the artificial tooth to be contacted with alveolar bone, a metal base member having an opening therein and disposed inside of and attached to said contacting member, a metal post inserted into said opening of the metal base member and at least two elastic buffer members disposed in a space between said metal base member and said metal post, said composite material having compatibility with living tissues containing 40 to 95% by weight of a calcium phosphate compound and 60 to 5% by weight of an organic polymer, each of said elastic buffer members being spaced apart for movably receiving said metal post by which pressure imposed upon the artificial tooth is transmitted, said metal base member being constituted by an upper section and a lower section removably connected to each other.

2. An artificial tooth according to claim 1 wherein said upper section and said lower section are threadedly connected to each other.

3. An artificial tooth according to claim 1 wherein a high polymer biocompatible material is affixed to a portion of the metal base member contacting with gingival mucosa.

4. An artificial tooth according to claim 1 wherein said elastic buffer member interconnects said metal base member and said metal post.

5. An artificial tooth according to claim 1 wherein said calcium phosphate compound is hydroxyapatite.

6. An artificial tooth according to claim 1 wherein said organic polymer is selected from the group consisting of polylactic acid, polyglycolic acid, polymethylmethacrylate, poly(trifluoroethyl methacrylate), polyethylene and polypropylene.

7. An artificial tooth according to claim 1 wherein an outer lateral side of said contacting member is formed by alternate projections and recesses.

8. An artificial tooth according to claim 7 wherein said alternate projections and recesses are arranged in a spiral form.

9. An artificial tooth according to claim 1 wherein said contacting member has a hemispherical bottom section.

10. An artificial tooth according to claim 1 wherein a crown is attached to said metal post.

* * * * *